(12) United States Patent
Fischer et al.

(10) Patent No.: US 11,771,305 B2
(45) Date of Patent: Oct. 3, 2023

(54) DEVICE WITH A WORKING CHANNEL GUIDING ELEMENT

(71) Applicant: Erbe Elektromedizin GmbH, Tuebingen (DE)

(72) Inventors: Klaus Fischer, Nagold (DE); Thomas Staebler, Tuebingen (DE); Charlotte Herrberg, Bodelshausen (DE); Achim Brodbeck, Metzingen (DE)

(73) Assignee: ERBE ELEKTROMEDIZIN GMBH, Tuebingen (DE)

( * ) Notice: Subject to any disclaimer, the term of this patent is extended or adjusted under 35 U.S.C. 154(b) by 947 days.

(21) Appl. No.: 16/210,395

(22) Filed: Dec. 5, 2018

(65) Prior Publication Data
US 2019/0167075 A1  Jun. 6, 2019

(30) Foreign Application Priority Data
Dec. 5, 2017  (EP) .................................... 17205535

(51) Int. Cl.
*A61B 1/00* (2006.01)
*A61B 1/005* (2006.01)
(Continued)

(52) U.S. Cl.
CPC ........ *A61B 1/00073* (2013.01); *A61B 1/0014* (2013.01); *A61B 1/0055* (2013.01);
(Continued)

(58) Field of Classification Search
CPC ............ A61B 1/00087; A61B 1/00098; A61B 1/00101
See application file for complete search history.

(56) References Cited

U.S. PATENT DOCUMENTS

| 6,010,515 A | 1/2000 | Swain |
| 6,878,106 B1 | 4/2005 | Herrmann |

(Continued)

FOREIGN PATENT DOCUMENTS

| DE | 10334100 A1 | 3/2005 |
| DE | 102006054218 A1 | 5/2008 |

(Continued)

OTHER PUBLICATIONS

Extended European Search Report dated Jun. 6, 2018, for EP Application No. 17205535.2 (7 pgs.).

(Continued)

*Primary Examiner* — Matthew J Kasztejna
(74) *Attorney, Agent, or Firm* — Fitch, Even, Tabin & Flannery LLP

(57) ABSTRACT

The device comprises an endoscope shaft through which extends a working channel ending at an outlet side of the shaft. A guiding element extends through the working channel, said guiding element being preferably guided in longitudinal direction in and along the working channel. The device is set up in such a manner that the distal end section of an instrument extending in longitudinal direction next to the shaft can be moved alongside the shaft beyond the outlet side in order to move the working section of the instrument away from the outlet side so as to lengthen the distal end section of the device. The instrument is coupled to the guiding element in order to guide the working section of the instrument in a transverse direction away from the outlet side in a region opposite the outlet side in order to work in the region with the instrument.

13 Claims, 6 Drawing Sheets

(51) Int. Cl.
*A61B 1/01* (2006.01)
*A61B 1/018* (2006.01)
*A61B 1/267* (2006.01)
*A61B 90/00* (2016.01)
*A61B 1/015* (2006.01)
*A61B 1/07* (2006.01)
*A61B 34/37* (2016.01)
*A61B 17/00* (2006.01)

(52) U.S. Cl.
CPC ...... *A61B 1/00087* (2013.01); *A61B 1/00098* (2013.01); *A61B 1/00133* (2013.01); *A61B 1/01* (2013.01); *A61B 1/018* (2013.01); *A61B 1/005* (2013.01); *A61B 1/015* (2013.01); *A61B 1/07* (2013.01); *A61B 1/267* (2013.01); *A61B 34/37* (2016.02); *A61B 90/361* (2016.02); *A61B 2017/00296* (2013.01)

(56) References Cited

U.S. PATENT DOCUMENTS

| | | | | |
|---|---|---|---|---|
| 7,575,548 | B2* | 8/2009 | Takemoto | A61B 1/018 600/122 |
| 7,670,282 | B2* | 3/2010 | Mathis | A61B 1/018 600/104 |
| 10,285,695 | B2 | 5/2019 | Jaworek et al. | |
| 10,791,911 | B2 | 10/2020 | Wales et al. | |
| 10,792,100 | B2 | 10/2020 | Brannan | |
| 2004/0039250 | A1 | 2/2004 | Tholfsen | |
| 2004/0230096 | A1* | 11/2004 | Stefanchik | A61B 1/012 600/106 |
| 2004/0249367 | A1* | 12/2004 | Saadat | A61B 1/2736 600/101 |
| 2005/0288550 | A1 | 12/2005 | Mathis | |
| 2006/0069304 | A1 | 3/2006 | Takemoto et al. | |
| 2006/0287572 | A1 | 12/2006 | Wimmer | |
| 2008/0183035 | A1* | 7/2008 | Vakharia | A61B 17/00234 600/104 |
| 2008/0312498 | A1 | 12/2008 | Moll | |
| 2010/0042078 | A1 | 2/2010 | Okada | |
| 2012/0165604 | A1 | 6/2012 | Stokes | |
| 2013/0041214 | A1 | 2/2013 | Maahs | |
| 2015/0335388 | A1 | 11/2015 | Iida | |
| 2017/0071653 | A1 | 3/2017 | Enderle | |

FOREIGN PATENT DOCUMENTS

| | | |
|---|---|---|
| DE | 202009009342 U1 | 11/2010 |
| DE | 102010020220 A1 | 11/2011 |
| EP | 1639936 A1 | 3/2006 |
| EP | 3141203 A1 | 3/2012 |
| JP | 2002-537011 A | 11/2002 |
| JP | 2006-087687 A | 4/2006 |
| JP | 2008-513043 A | 5/2008 |
| JP | 2008-284107 A | 11/2008 |
| JP | 2017-525461 A | 9/2017 |
| JP | 2019-522512 A | 8/2019 |
| RU | 2672520 C2 | 11/2018 |
| WO | 2010/118054 A2 | 10/2010 |
| WO | 2018/006044 A1 | 1/2018 |

OTHER PUBLICATIONS

Indian Office Action dated Feb. 21, 2022, in corresponding Indian Application No. 201814044426 (6 pages).
Russian Office Action and Search Report dated Nov. 16, 2021, in corresponding Russian Application No. 2018141805/14(069626), with machine English translation (21 pages).
Office Action dated May 26, 2022, in corresponding JP Application No. 2018-211914 (19 pages).

* cited by examiner

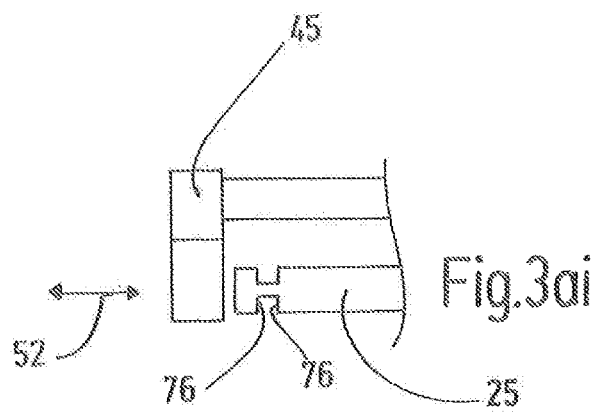
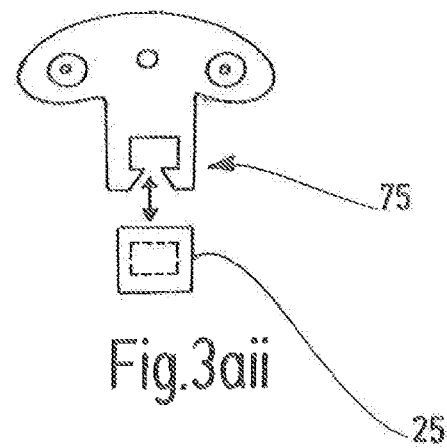
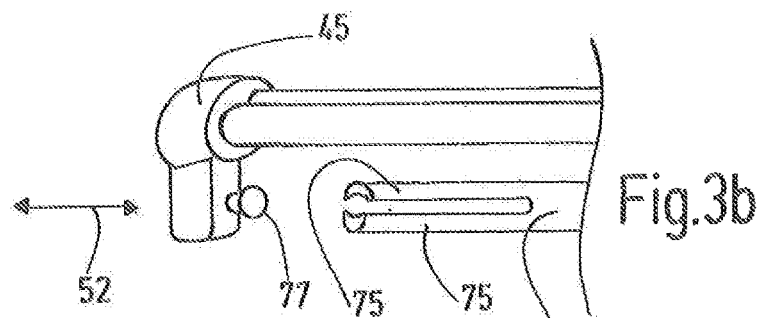
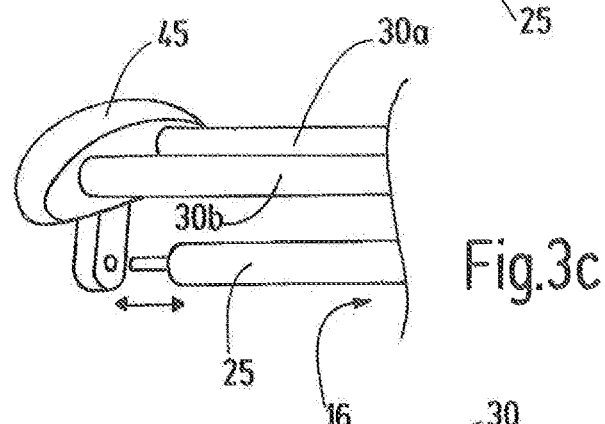
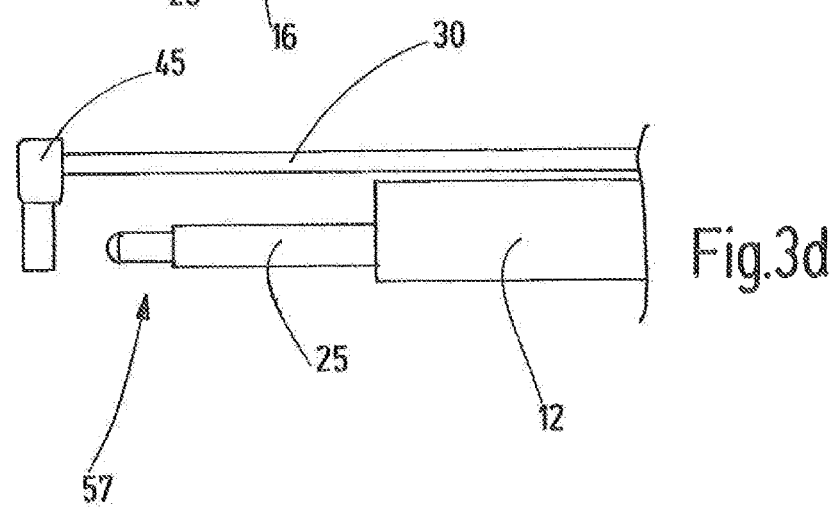

DEVICE WITH A WORKING CHANNEL GUIDING ELEMENT

RELATED APPLICATION(S)

This application claims the benefit of European Patent Application No. 17205535.2, filed Dec. 5, 2017, the contents of which are incorporated herein by reference as if fully rewritten herein.

TECHNICAL FIELD

The invention relates to a device with an endoscope and an instrument guided by means of the endoscope.

BACKGROUND

Prior art has disclosed devices comprising an endoscope having a working channel through which extends an instrument beyond the distal end of the endoscope, wherein the instrument is guided in longitudinal direction in the working channel. Publication DE 103 34 100 A1, for example, describes an endoscope with a section of a working channel that can be bent for such a purpose.

An endoscope has been known from publication DE 10 2006 054 218 A1, wherein a guidewire extends through the endoscope's working channel, wherein an occluder is connected to a guidewire at the distal end in the guiding channel, said occluder being movable out of the guiding channel by means of the guidewire for closing an incision.

In other devices, the instrument is guided on the outside of the endoscope.

Referring to the device disclosed in publication EP 3 141 203 A1, an ablation instrument extends, for example, along the shaft of an instrument through a lumen of a sheath that provides another lumen for the endoscope. Furthermore, the ablation instrument extends through a fitting that is fastened to the distal end of the shaft of the endoscope. The ablation instrument can be moved in the lumen of the sheath and in the fitting along the shaft of the endoscope.

From publication DE 10 2010 020 220 A1 a guiding cuff has been known which can be fastened to a longitudinal side of the shaft of an endoscope in order to guide endoscopic instruments next to the endoscope through the guiding cuff.

Publication DE 20 2009 009 342 U1 describes an endoscope having a flexible endoscope shaft, in which case an inflatable tube is arranged on the longitudinal side of said flexible endoscope shaft.

It is the object of the present invention to state an improved device comprising an endoscope and to state an instrument guided by means of the endoscope.

SUMMARY

This object is achieved with a device as described herein.

The device according to one embodiment of the invention comprises an endoscope with a shaft, said shaft containing at least one working channel. The working channel ends on one side (outlet side) of the shaft, preferably on the front side of the endoscope on the distal end of said endoscope. Preferably, the shaft is flexible. The device comprises at least one instrument that is arranged so as to extend next to the shaft. The device is designed in such a manner that a distal end section of the instrument containing the working section of the instrument can be moved along the shaft beyond the side of the shaft where the working channel ends in order to move the working section of the instrument into a region opposite (in front of) the side of the shaft in order to work with the working section in this region during the endoscopic use of the device. The region can preferably be viewed with the aid of a means of the endoscope for image transmission. The instrument is in engagement with a guiding element in order to guide the working section of the instrument by means of the guiding element, while the end section is being moved beyond the side of the shaft into the region. For guiding the section of the instrument, the guiding element extends—while the distal end section is being moved—beyond the side of the shaft through the working channel. Preferably, the guiding element is guided so as to be longitudinally movable in the working channel in order to—with the shaft—form a telescopic guide for the working section of the instrument arranged along the longitudinal side of the shaft.

The fact that the instrument is guided by means of the guiding element comprises that the guiding element is movably coupled to the instrument in such a manner, that— during a movement of the guiding element that is movably guided in the working channel in a longitudinal direction— the guiding element is also moved, and/or that the guiding element—during a movement of the instrument along the shaft—is also moved with the instrument, in which case the guiding element guided in a longitudinally movable manner in the working channel—conveys to the instrument the guiding of the guiding element in the working channel. Alternatively or additionally, the feature that the instrument is guided according to one form of the invention by means of the guiding element may comprise that—on the guiding element—a guide for guiding the instrument outside the working channel is arranged, in which case the guide is arranged preferably opposite the side where the working channel leaves the shaft, and in which case the instrument is in engagement with the guide.

Compared to known devices, the device according to one form of the invention allows a more stable guiding of the instrument arranged outside the endoscope and thus, for example, a more smooth positioning and/or orientation of the working section of the instrument in the region in which the instrument is to be used, for example relative to the tissue to be treated and/or examined with the instrument.

The device according to some embodiments of the invention is preferably further developed to exhibit at least one of the features described hereinafter:

The device is preferably set up in such a manner that the guiding element can be moved forward along the working channel in distal direction and/or retracted in proximal direction, and/or that the guiding element can be rotated in the working channel, in which case the movement of the guiding element is transmitted to the instrument by a motion coupling of the guiding element with the instrument. In doing so, the guiding element can be operated, preferably outside the body of the patient for moving the instrument by means of the guiding element, while the distal end of the device with the working section is located inside the body.

Preferably, the instrument is movably coupled to the guiding element, so that a forward movement of the guiding element in the working channel in longitudinal extension direction of the working channel in the direction toward the outlet side is converted into a movement of the working section of the instrument away from the outlet side. Preferably, the forward movement is converted into a movement of the working section into longitudinal extension direction of the working channel away from the front side. Alternatively or additionally, the instrument is preferably coupled to the guiding element in such a manner that a retraction of the guiding element in the working channel in longitudinal extension direction of the working channel in the direction toward the proximal end of the device is converted into a movement of the working section of the instrument back, closer to the shaft. The working section can be shifted forward and/or pulled forward by introducing a force into the guiding element, preferably in distal direction. Additionally or alternatively, the working section can preferably be retracted and/or slid back in proximal direction by introducing a force into the guiding element.

The device is preferably set up in such a manner that the guiding element can be rotated in the working channel about the longitudinal axis of the guiding element, in which case the rotary motion is transmitted to the working section due to the coupling of the guiding element to the instrument, in order to move and/or pivot the working section about an axis. The working section of the instrument can preferably be driven via the guiding element to perform a rotation and/or a pivoting motion about the longitudinal axis of the guiding element. Alternatively or additionally, the instrument is movably coupled to the guiding element in such a manner that the working section of the instrument is pivoted when a section of the guiding element projecting from the outlet side and extending from the shaft is pivoted relative to the shaft opposite the front side about an axis transverse with respect to the longitudinal extension direction of the guiding element.

The guiding element may be a flexible guiding rod. A hollow space may extend through the guiding element along the guiding element. Accordingly, the guiding element may comprise, for example, a flexible tube and/or tubing. For example, the guiding element may comprise a wire or a cluster of wires. The wire or wires may extend along the working channel. Alternatively or additionally, the guiding element may comprise a wire coil, for example. For example, the guiding element may consist of plastic and/or metal.

At least one of the instruments guided by means of the guiding element may be a sampling instrument and/or an application instrument for the application of fluid, in particular gas and/or liquid, and/or solids to the tissue and/or into the tissue, a suction instrument and/or a surgical cutting and/or coagulation instrument. At least one instrument guided by means of the guiding element and arranged so as to extend next to the shaft, may be—alternatively or additionally—a measuring instrument for regulating, controlling, measuring or detecting tissue parameters. Alternatively or additionally, an instrument guided by means of the guiding element may be disposed for transmitting energy to the distal end of the device, for example.

At least one of the instruments guided by means of the guiding element may be a coagulation probe, a surgical fluid jet probe for lifting (elevation) tissue by introducing fluid, in particular liquid, under the tissue, a cryoprobe, for example a cryoprobe for freezing and taking a tissue sample, a sample excision forceps, an introduction cannula, a foreign body and/or stone catcher, a brush and/or a suction catheter.

The function of the guiding element may be restricted to providing a guide for the one or more instruments that are in engagement with the guiding element and/or to the transmission of movements to the one or several instruments that are in engagement with the guiding element. Alternatively, the guiding element is itself a medical instrument. In particular, the guiding element may comprise a working section intrinsic to the guiding element. For example a channel may extend through the guiding element for conducting fluid, in particular liquid and/or gas, and/or a solid. The channel extending through the guiding element may be determined for the evacuation of fluid, in particular liquid and/or gas, and/or solids from the distal end of the channel and/or for the transport of fluid, in particular liquid and/or gas, and/or a solid to the distal end and out of the distal end.

Preferably, the instrument comprises at least one functional element that extends next to the shaft of the endoscope up to the working section of the endoscope. The functional element is preferably disposed for guiding and/or moving the instrument, in particular its working section, and/or for actuating the instrument and/or for conveying media such as, for example, fluid, in particular liquid and/or gas, solids and/or electrical power to the working section and/or away from the working section. Preferably, the functional element is set up in such a manner that the user of the device can move and/or guide and/or use and/or supply the instrument by means of the functional element, wherein the handling and/or supply of the instrument by means of the functional element may preferably be done from outside the body of the patient, while the working section of the instrument is located in the body of the patient.

Preferably, in addition to the guiding function by means of the guiding element, there is arranged on the longitudinal side of the shaft a guide that is disposed for guiding the instrument along the longitudinal side of the shaft. The guide is in engagement with the instrument, preferably with the functional element of the instrument that extends up to the working section of the instrument along the shaft. Preferably, the functional element is guided on the shaft by means of at least one guide holder that is arranged so as to be effective at least between the longitudinal side of the shaft and the instrument. For example, a guide holder can be fastened to the shaft. Alternatively, for example, a guide holder is fastened to the functional element. For example, the guide holder may be a guide ring that is fastened to the shaft or the functional element and through which extend the shaft and/or the functional element.

Preferably, the guiding element has at least one engagement section for coupling the guiding element to an instrument. Preferably, the guiding element is disposed for coupling two or more instruments. Preferably, the guiding element has one engagement section each for two or more instruments.

Alternatively or additionally, an engagement element may be fastened to the guiding element, in which case the guiding element can be coupled by means of the engagement element to at least one instrument.

Preferably, the instrument is in engagement with engagement element and/or the engagement section in such a manner that the instrument can be shifted, relative to the engagement element and/or the engagement section, in the engagement element and/or the engagement section. Consequently, the engagement element preferably provides—by means of the engagement element and/or by means of the engagement section—a guide for the instrument outside the shaft opposite the outlet side, from where the guiding element moves out of the shaft.

Preferably, the engagement element and/or the engagement section has a form matching the outer form of the distal end of the shaft and/or a form matching the holding element arranged on the distal end of the shaft, so that the engagement element and/or the engagement section assume a specific orientation and/or a specific position relative to the distal end of the shaft and/or relative to the holding element when the matching form is in engagement with the outer form. For example, on the distal end of the shaft there is provided and/or formed a fitting for the engagement element and/or the engagement section, in which case the engagement element and/or the engagement section can be moved in axial direction into the fitting and in which case the rotatability of the engagement element and/or the engagement section in the fitting is restricted. Preferably, the device is designed in such a manner that the outer form and the matching form will automatically come into engagement when the engagement section and/or the engagement element are moved back in the direction toward the shaft.

The engagement between the guiding element and the instrument can preferably be released in a non-destructive manner. Particularly preferably, the device is designed in such a manner that the engagement between the guiding element and the instrument can be released from outside the body of the patient in a non-destructive manner and/or that a non-destructively releasable engagement between the guiding element and the instrument can be provided from outside the body of the patient, when the distal end of the device having the working section is located in the body of the patient.

Preferably, a guide holder is fastened to the distal end of the shaft, said guide holder providing a guide along the shaft for the instruments extending along the shaft. To do so, the guide holder preferably has receptacles in which respectively one instrument is guided so as to be slidable, preferably along the longitudinal extension of the distal end of the shaft. Preferably, the device is designed in such a manner that one or more instruments can be brought into engagement with the guiding element in order to move said instruments while at least another instrument arranged in its receptacle is out of engagement with the guiding element.

Preferably, the guiding element is designed for the accommodation of at least two instruments that extend next to the shaft in such a manner that the working section of at least one of the instruments can be shifted, guided by means of the guiding element, relative to the working section of another instrument. Alternatively or additionally, the guiding element is designed for the accommodation of at least two instruments that are arranged so as to extend next to the shaft in such a manner that the working section of at least one of the instruments can be rotated and/or pivoted relative to the working section of the other one of the instruments by means of the guiding element. Preferably, the device for using the guiding element for shifting, rotating and/or pivoting one of the instruments relative to the other instrument is set up from outside the body of the patient when the working sections of the instruments are located in the body of the patient.

In accordance with a form of the invention, there is also stated a guiding element that is disposed for the use in a device according to the invention as described herein, for example.

BRIEF DESCRIPTION OF THE DRAWINGS

Additional advantageous features of the device according to the invention can be inferred from the description, the figures and the dependent claims hereinafter.

They show schematically in

DETAILED DESCRIPTION

Figure 1A:
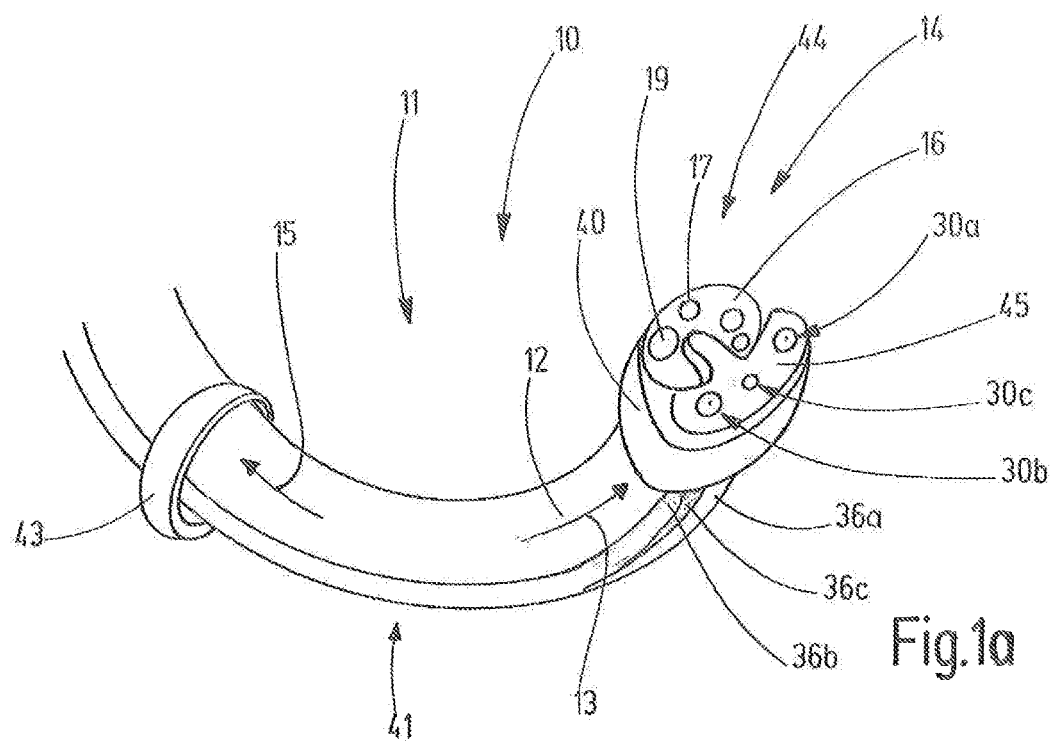
FIGS. 1a to 1d—partially perspective views of exemplary embodiments of the device according to the invention, FIG. 1e—a partially perspective representation of another exemplary embodiment of the device according to the invention, FIG. 2a—a partially perspective representation of another exemplary embodiment of the device according to the invention with a guide holder fastened to the endoscope with receptacles for the instruments, FIG. 2b—a partially perspective representation of an exemplary embodiment of an arrangement of an endoscope and a guiding element of an exemplary device according to the invention, wherein the guiding element is used for indirectly moving at least two instruments via the guiding element relative to each other, FIG. 2c—a partially perspective representation of an exemplary embodiment of the device according to the invention with a guiding element and an instrument that can be moved relative to said guiding instrument, FIGS. 3ai to 3d—perspective representations of various options of coupling the guiding element to the engagement element or the instrument, respectively, and FIG. 4—an exemplary handle for a device according to the invention.
Figure 1B:
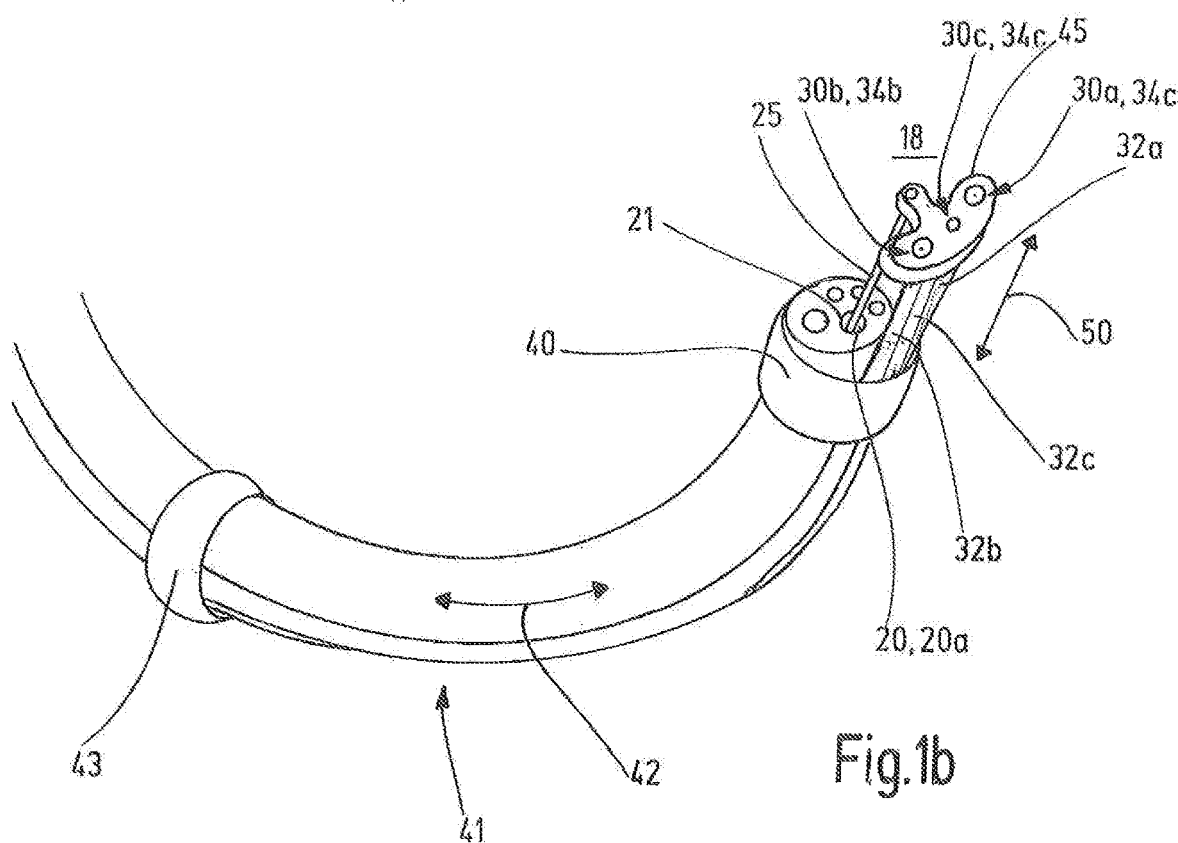

FIGS. 1a, 1b show a partially perspective representation of an exemplary embodiment of the device 10 according to the invention. The device 10 comprises an endoscope 11 with a flexible shaft 12. The shaft 12 defines a distal direction 12 (sense of direction) along which the shaft 12 extends from its proximal end (not illustrated) to its distal end 14. Conversely, the shaft 12 defines a proximal direction 15 from its distal end 14 along the shaft 12 up to its proximal end. On the distal end 14 on the front side 16 of the shaft 12, there is arranged an illuminating unit 17 for illuminating a region 18 relative to the front side 16 of the shaft 12. Extending through the shaft 12, there is a means for transmission of an image up to an input 19 of the means in the front side 16, where, for example, a lens system belonging to the means for image transmission may be arranged. The means for the transmission of an image of the region 18 to be examined and/or treated is provided opposite the front side 16 of the shaft 12 in order to be able to visually monitor the examination and/or treatment in the region 18 opposite the front side 16 by means of the endoscope 11 from outside the body of the patient. Additional lines for transmission in proximal direction and/or distal direction, for example of signals, electrical output, gases, in particular fluids and/or gas, or solids, may extend through the shaft 12 up to the front side 16. In any event, at least one working channel 20 extends through the shaft 12 up to an opening 21 in the front side 16 of the shaft 12. For example, in a known device 10, it is possible to slide an instrument, for example, a tool, a gripper through such a working channel out of the front side 16 of the shaft 12 in order to use it to perform in this region—with the aid of the means for image transmission and visual control by the surgeon—examinations and/or treatments in the region 18.

In the inventive device 10 (see in particular FIG. 1b), a longitudinal guiding element 25 extends through the working channel 20, said guiding element being movably guided in longitudinal direction 26 of the working channel 20. The guiding element 25 moves through the opening 21 in the front side (outlet side) out of the working channel 20. The guiding element 25 extends in proximal direction 15 preferably up to a proximal end of the device 10 (not shown in FIGS. 1a, 1b), from where the guiding element 25 can be actuated, in particular moved, by a surgeon.

The device 10 according to the invention comprises at least one instrument 30 that extends along the shaft 12 next to the shaft 12. In the depicted exemplary embodiment, the inventive device 10 comprises a first instrument 30a and a second instrument 20b, which each may be a coagulation probe having respectively one electrode for igniting a plasma, and a third instrument 30c which may be, for example a water jet probe. Each of the instruments 30a, 30b, 30c has respectively one distal end section 32a-c with a working section 34a-c on the distal ends of the instruments 30a, 30b, 30c.

At least one functional element 36a-c per instrument 30a, 30b, 30c extends along the shaft 12 relative to the working section 34a-c. The functional elements 36a-c extending next to the shaft can be used for guiding and/or moving the respective instrument 30a-c or the working section 34a-c and/or for actuating the instrument 30a-c and/or transmitting media to the working section 34a-c of the instrument 30a-c and/or of the working section 34a-c, away from the distal end of the instrument 30z-c. The user of the device 10 can move, guide, operate and/or supply the instrument 30a-c via the functional element 36a-c, for example. If the first and the second instruments 30a, 30b are an APC probe, the first instrument 30a and the second instrument 30b being the functional element 36a, 36b may each comprise, for example a tubing through which extends an electrical line that is connected to the electrode, wherein argon gas can be conveyed to the working section 34a, 34b of the APC probe with its electrode in order to ignite an argon plasma in front of the distal end of the APC probe. If the third instrument 30c, as in the depicted exemplary embodiment, is a liquid jet probe, this comprises as the functional element 36c, for example a tubing that is connected to an outlet of the liquid jet probe in the working section 34c of the probe on its distal end and is disposed to supply a liquid to the outlet.

In the depicted exemplary embodiment, the functional elements 36a-c of the instruments 30a-c extend though a guiding cuff 40 fastened to the distal end 14 of the shaft 12, said cuff forming a first guide holder 40 of the device 10 for guiding the instruments 30a, 30b, 30c on the outside of the shaft 12 in longitudinal direction 42. In proximal direction 15 from the distal end 14 and the first guide holder 40, there extend the functional elements 36a-c through the second guide holder 43 arranged on the longitudinal side 41 of the shaft 12, said second guide holder 43 being disposed to guide the functional elements 36a-c on the longitudinal side 41 of the shaft 12. The second guide holder 43 may be, for example, a ring that encloses the shaft 12 and/or the functional elements 36a-c. The second guide holder 43 may be affixed to the shaft 12 against the axial movement along the shaft 12 or affixed to the functional element 36a-c against an axial movement of the second guide holder 43 relative to the functional element 36a-c. In addition to the two guide holders 40, 43 depicted as examples for guiding the instrument(s) 30a, 30b, 30c extending laterally next to the shaft 12, at least one other guide holder (not illustrated) may be provided outside on the shaft 12 for guiding the instrument (s) 30a, 30b, 30c. Embodiments with only one guide holder effective between the longitudinal side 41 of the shaft 12 and the instrument(s) 30a, 30b, 30c is (are) possible for guiding the instruments 30a, 30b 30c on the shaft along the longitudinal side 41 of the shaft 12.

The first guide holder 40 arranged on the distal end 14 of the shaft 12 may form a sliding element via which the device 10 rests on the tissue section in order to facilitate the maintenance of a defined distance of the working section of at least one instrument 30a, 30b, 30c from the tissue.

Additionally or alternatively to the first and/or second guide holders 40, 43, the device 10 may comprise a plastic tubing (not illustrated), in which case the shaft 12 and the functional elements 36a-c extend through the plastic tube, and in which case the plastic tube preferably provides a lumen for the shaft 12 and a separate lumen for the functional elements 36a-c, and in which case the functional elements 36a-c are guided in the lumen for the functional elements 36a-c along the shaft 12 of the endoscope 11. The plastic tubing may additionally be disposed for smoke evacuation.

The instruments 30a-c are coupled—on the distal end 44 of the device 10 comprising the guide element 25 that extends through the working channel 30—to an engagement section of the guiding element 25 and/or to an engagement element 45 coupled to the guiding element 25 in such a manner that the instruments 30a, 30b, 30c are guided—during a movement of the working section 34a-c-away from the front side 16 of the shaft 12 in the region opposite (relative to) the front side 16 and/or back to the front side 16 out of the region 18 by the guiding element 25, guided during the movement in the working channel 20. To do so, the section of the guiding element that projects distally from the front side 16 and into the working channel 20 is rigid or, preferably, flexible in order to guide the instruments 30a, 30b, 30c.

The device 10 is constructed in such a manner that the counter-constraint forces are discharged into the shaft 12—due to the guiding of the instruments 30a, 30b, 30c via the guiding element 25—through the wall surface delimiting the channel 20 and enclosing the channel 20. Therefore, the guiding element 25 may brace itself within the working channel 20 against the shaft 12 and thus convey to the instrument 30a, 30b, 30c arranged next to the shaft 12 the guiding motion of the guiding element 25 in the working channel 20. This means that the instrument is indirectly guided opposite the outlet side 16 outside the working channel 20 via the guiding element 25 with the working channel 20. The shaft 12 and the guiding element 25 thus form a telescopic guide for the working section 34a-c of the instruments 30a, 30b, 30c extending along the longitudinal side 41 of the shaft 12. Inasmuch as, in the device 10 according to the invention, the working channel 20 is used indirectly via the guiding element 25 for guiding the working sections 34a-c relative to the outlet side 16, the working sections 34a-c can be guided in front of the outlet side 16 in a more stable manner and thus in a safer and smother manner than in known devices.

The device 10 according to the invention is preferably set up in such a manner that the user is able to transmit the force in the direction of movement for moving the working sections 34a-c of the instruments 30a, 30b, 30c into the region 18 opposite the front side 16 and/or out of the region 18 to the working sections 34a-c via the guiding element 25. Preferably, the device 10 is set up in such a manner that the user can control the guiding element 25 on the grip (not shown in FIGS. 1a, 1b; see, e.g., FIG. 4) in order to transmit a force for moving the working sections 34a-c into the region 18 and/or out of the region 18, along the guiding element 25 toward the instruments 30a, 30b, 30c. The device 10 is set up in such a manner that the user can control the guiding element 25 from outside the body of the patient in order to introduce the force for pushing and/or pulling the instruments 30a, 30b, 30c—back out of the region 18 and/or forward into the region 18—via the guiding element 25. While pushing and/or pulling the instruments 30a, 30b, 30c via the guiding element 25, it may be necessary to push the functional elements 36a-c (lines) of the instruments 30a, 30b, 30c from outside the body of the patient further forward or to retract them.

In order to achieve a direct transmission of a pushing movement of the actuated section 48 of the guiding element 25, e.g., on the handle, toward one or several instruments 30a, 30b, 30c, the guiding element 25 is preferably pressure-resistant and is coupled—preferably in a pressure-resistant manner—to the working section 34a-c of the instrument 30a, 30b, 30c. Furthermore, the guiding element 25 that acts as a pushing member is guided in the working channel 20, preferably in a rigid manner.

In order to achieve a direct transmission of a pulling movement of the guiding element 25 on the handle to the instrument 30a, 30b, 30c, the guiding element 25 preferably displays tensile stiffness and preferably is coupled to the working section 34a, 34b, 34c of the instrument 30a, 30b in manner displaying tensile stiffness.

The end section 20a of the working channel 20 at the opening 21 in the front side 16 specifies—with its longitudinal extension direction—a guiding direction 50 for the guiding element 25 and thus the working sections 34a, 34b 34c of the instruments 30a, 30b, 30c, along which the guiding element 25 and, moreover, also the working sections 34a, 34b, 34c of the instruments, away from the front side 16 into region 18 and back. The distal end sections 32a-c of the instruments 30a, 30b, 30c, as shown by FIG. 1b, can be moved in guiding direction 50 along the longitudinal extension direction of the distal end section of the working channel 20—by introducing a force into the guiding element 25—away from the distal end 14 of the shaft 12 (can be pushed forward and/or pulled forward) and/or can be moved back toward the distal end 14 of the shaft 12 (can be pushed back and/or pulled back).

Alternatively or additionally to the introduction of force into the guiding element 25 for moving the instruments 30a, 30b, 30c extending next to the longitudinal side 41 of the shaft 12, the device 10 may be set up in such a manner that a force is transmitted in the guiding direction 50 for moving the instrument along the longitudinal extension direction of the end section of the working channel 20 toward the working sections 34a-c of the instruments 30a, 30b, 30c—completely or partially via at least one of the functional elements 36a-c. In such cases, the user can, for example, slide the functional elements 36a-c along the shaft 12 in distal direction 13 in order to move the sections 32a-c of the instruments 30a, 30b, 30c having the working sections 34a, 34b, 34c beyond the front section 16 in the direction toward the region 18 in which an operation is to be performed with the working sections 34a-c.

Figure 1C:
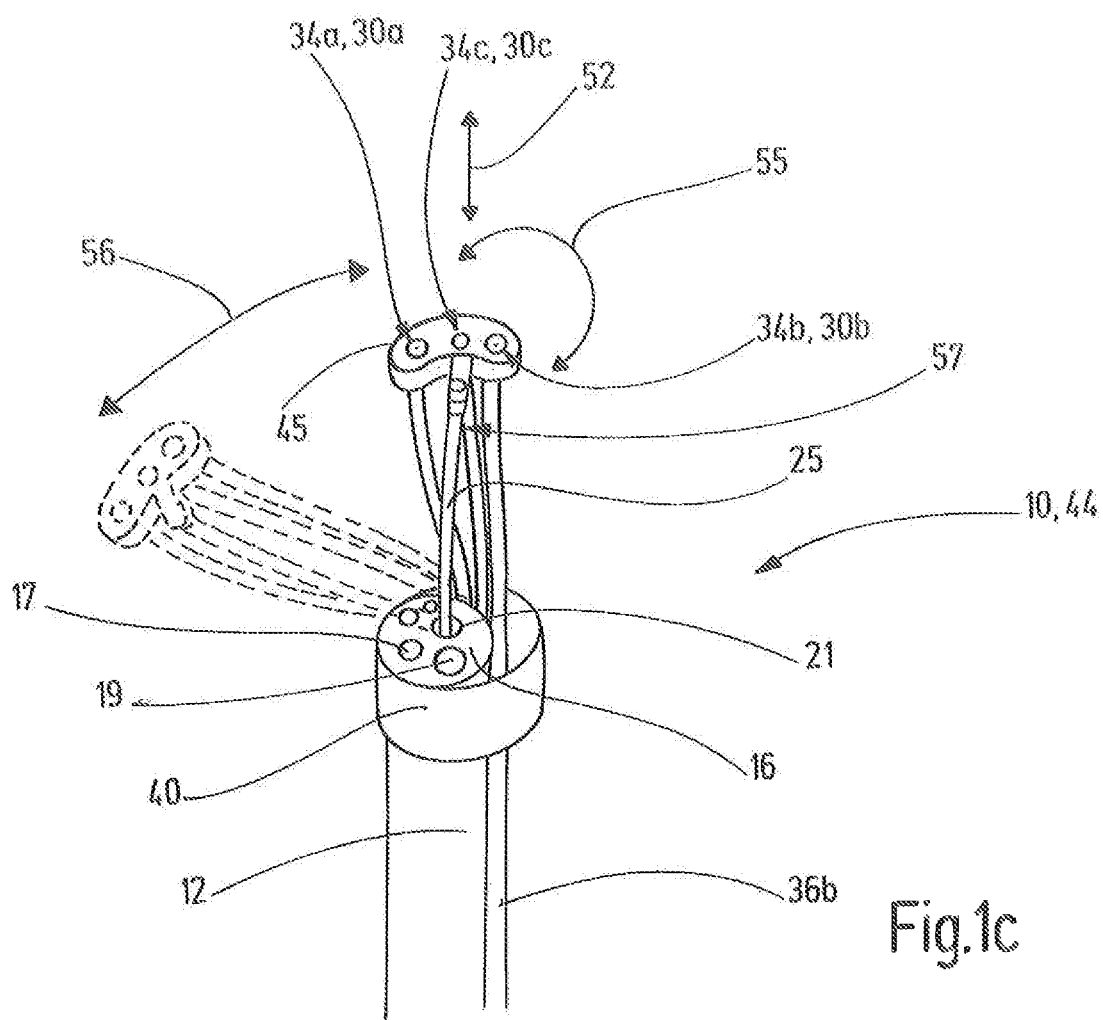

FIG. 1c shows an exemplary embodiment of the device 10 according to the invention that, in accordance with the example, is set up in such a manner that the working sections 34a-c can be rotated and/or pivoted relative to the shaft 12 about an axis through the guiding element 25 extending along the longitudinal extension direction 52 of the guiding element 25, as is indicated by the double arrow 55. This also includes a rotation and/or a pivoting at an angle of rotation and/or a pivoting angle between a starting position and an end position, said angle being smaller than 360°. The device 10 is preferably configured in such a manner that the torque for rotation and/or pivoting can be transmitted to the working sections 34a, 34b, 34c, via the guiding element 25. Preferably, the guiding element 25 can be controlled for the rotation of the working sections 34a, 34b, 34c and/or for pivoting these outside the body of the patient, when the distal end 44 of the device 10 is located in a lumen of the body. To do so, the guiding element 25 is preferably torsion-proof at least in one direction of rotation—restricted to one direction of rotation or in both directions of rotation—in order to achieve a direct transmission of a movement of rotation of the guiding element 25 to the instruments 30a, 30b, 30c.

As can be inferred from FIG. 1c based on the double arrow 56 and the dashed line representation of the section of the guiding element 25 projecting from the opening 21, the engagement element 45 and the instruments 30a, 30b, 30c in a pivoted position, the working sections 34a, 34b, 34c arranged opposite the front side 16 are—in the exemplary embodiment according to the invention—pivotable relative to the distal end 14 of the shaft around an axis extending in transverse direction, for example perpendicular direction, with respect to the guiding element 25 in order to change the orientation of the working sections 34a, 34b, 34c arranged opposite the front side 16. The device 10 is preferably configured in such a manner that the torque for pivoting toward the instruments 30a, 30b, 30c can be transmitted via the guiding element 25. For example, the guiding element 25 may comprise one or more wires (not illustrated) coupled to the distal end 57 of the guiding element 25, said wires extending through a handling section of the device, for example on the grip of the device, so that the user of the device 10 can control the wires from outside the body of the patient, when the distal end 44 of the device 10 is located inside the lumen of a body of the patient. For example, the guiding element 25 may consist of a highly flexible tube, in which case the wires can extend from the proximal end of the device 10 to the distal end 57 of the guiding element 25 through the tube.

Figure 1D:
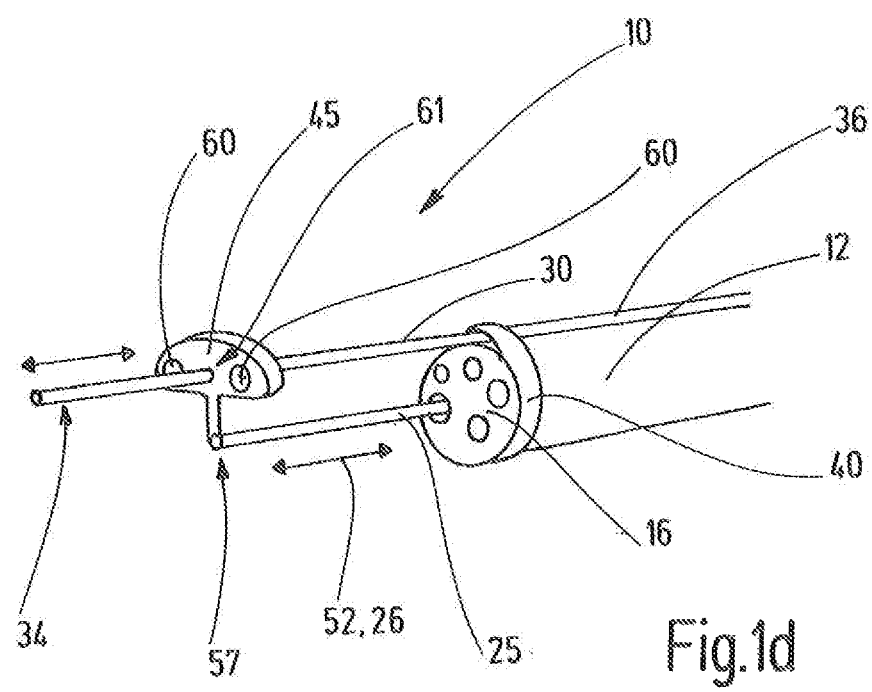

FIG. 1d shows another exemplary embodiment of the device 10 according to the invention with an engagement element 45 coupled to the guiding element 25 that may have at least one receptacle 60 for an instrument in order to couple the instrument to the guiding element 25 via the engagement element 45 in such a manner that a force introduced into the guiding element 25 in longitudinal extension direction of the guiding element 25 is transmitted to the instrument (which is not depicted here for the sake of clarity). The engagement element 45 has a receptacle 61 for another instrument 30, said receptacle being disposed to guide the other instrument 30 in a sliding manner, preferably along the longitudinal extension direction 52 of the section of the guiding element 25 projecting distally from the opening, in the engagement element 45 opposite the front side 16 relative to the guiding element 25. As an alternative to an engagement element 45 coupled to the guiding element 25, it is also possible for an engagement section of the guiding element 25 to have such a receptacle for an additional instrument 30. The guiding element 25 forms a guide arm projecting beyond the front side 16 held in the working channel 20 for the additional instrument 30 that can be moved relative to the guiding element 25 and provides, with the engagement element 45 or the engagement section, a guide for the additional instrument 30 that can be positioned relative to (in front of) the front side 16. The guiding element 25 is guided in the working channel 20 along the longitudinal extension direction of the working channel 20 in such a manner that the distance of the engagement element 45 or the engagement section—and thus the distance of the guide for the additional instrument 30—can be changed relative to the front side 16. The device 10 can be set up in such a manner that the force for sliding the working section 34 of the additional instrument 30 relative to the guiding element 25 toward the working section 34 via the functional element 36 of the instrument 30 can be introduced. To do so, the functional element 36 may be guided next to the longitudinal side of the shaft through a guide holder 40. The additional instrument 30 may be a liquid jet probe, for example. Such a probe can be configured to introduce liquid under a tissue layer in order to elevate it. In doing so, the distal end of the liquid jet probe is placed on the tissue. With the use of the exemplary embodiment of the device according to the invention, the distal end of the liquid jet probe may be placed on the tissue at a distance from the engagement element 45 and the front side 16. It is also possible to move forward into tight lumens of the body of the patient with the application of the distal working section 34 of the additional instrument 30 beyond the distal end of the guiding element 25, away from the distal end 57 of the guiding element 25.

Figure 1E:
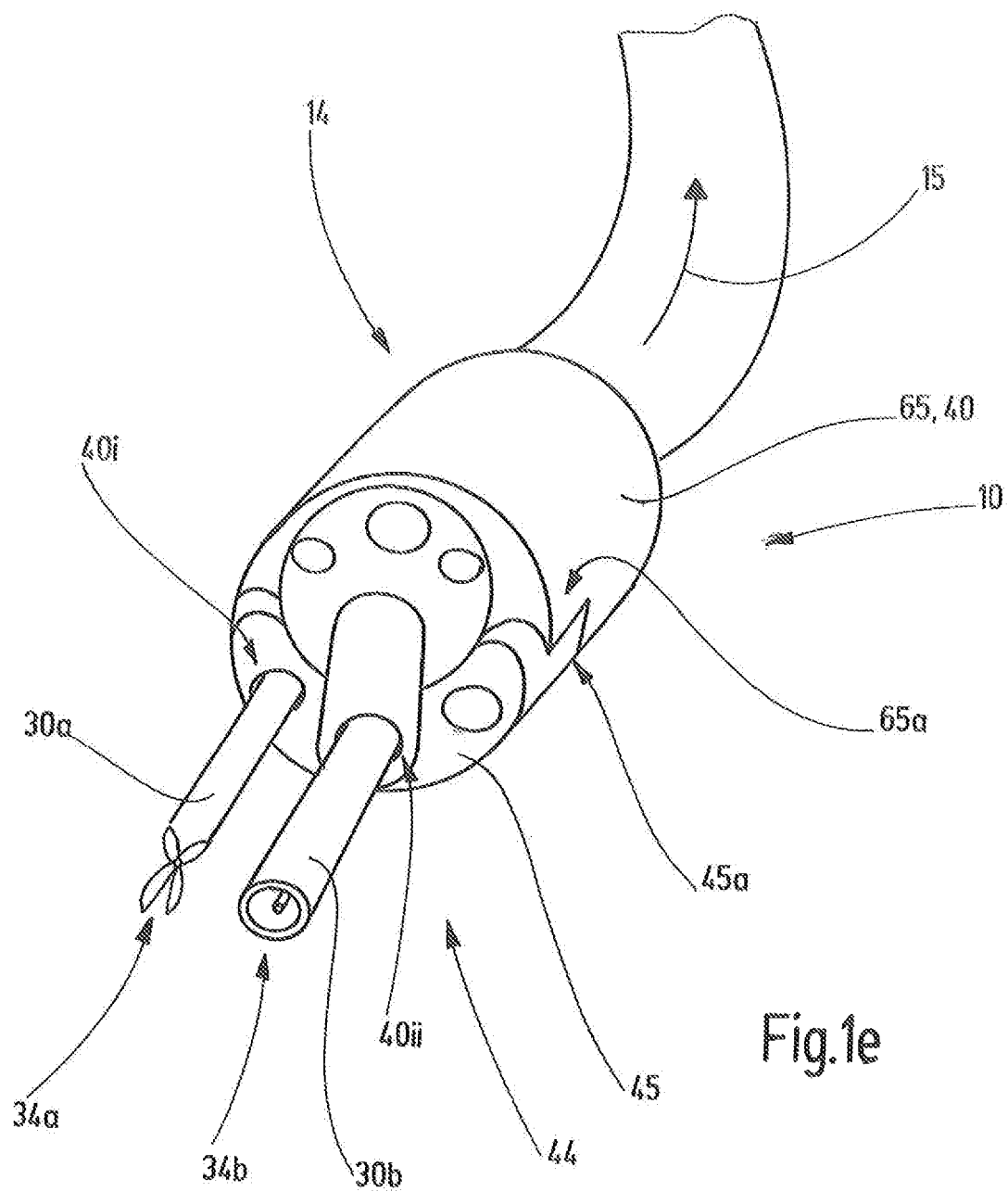

FIG. 1e is a partial perspective representation of another exemplary embodiment of the device 10 according to the invention, with a view onto the distal end 44 of the device 10. A holding element 65 having a positive-locking section 65*a* is mounted to the distal end 14 of the shaft 12. The positive-locking section 65*a* has a form that is complementary to a form-locking section 45*a* of the engagement element 45. FIG. 1e shows the engagement element 45 in retracted position arranged on the shaft 12, so that the positive-locking section 45*a* of the engagement element 45 is in engagement with the positive-locking section 65*a* of the holding element 65. The form-locking feature has the effect that the engagement element 45 is arranged about the shaft 12 in a torque-proof manner on the holding element 65, and that the engagement element 45 can no longer be moved back in proximal direction 15 relative to the distal end 14 of the shaft 15. Thus the holding element 65 defines a specific orientation and position of the engagement element 45 on the shaft 12 in the retracted position. At the same time, the holding element 65 may act as a guide for the instruments 30*a*, 30*b* on the shaft. For example, the holding element 65 may be a first guide holder 40 with at least two separate receptacles 40*i*, 40*ii* for one instrument 30*a*, 30*b*, respectively. For example, the instrument 30*a* may have a working section 34*a* with a gripper. For example, the instrument 30*b* may be an APC probe with a working section 34*b* with an electrode in order to generate an argon plasma.

Preferably, guiding and counter-guiding surfaces (not shown) are provided on the holding element 65 and the engagement element 45, said surfaces coming into engagement with each other on the shaft 12 when the engagement element 45 is retracted in such a manner that the positive-locking section 45*a* of the engagement element 45 automatically enters into positive-locking mode with the positive-locking section 65*a* of the holding element 65 mounted to the distal end 14 of the shaft 12. In this manner, it is possible to automatically adjust the position and the orientation of the engagement element 45 on the shaft 12 by means of the holding element 65 when the engagement element 45 is moved back out of a specified position opposite the front side 16.

Figure 2A:
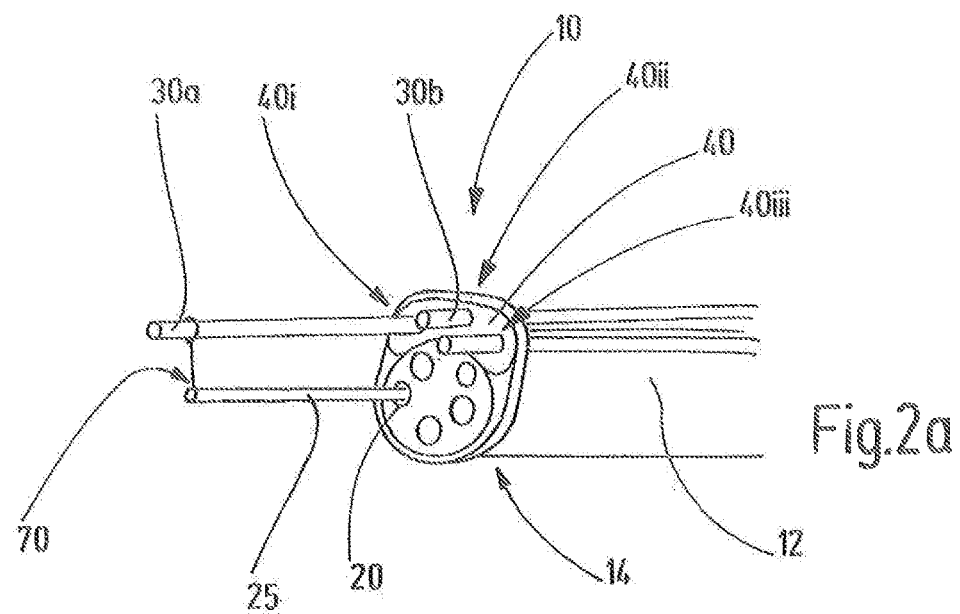

FIG. 2a shows, in a sectional perspective view, an exemplary embodiment of the device 10 according to the invention with a guide holder 40 mounted to the distal end 14 of the shaft 12, said guide holder having receptacles 40*i*, 40*ii*, 40*iii* in which one instrument 30*a*, 30*b*, 30*c*, respectively, is arranged in a guided manner. The instruments 30*a*, 30*b*, 30*c* are slidably guided in the receptacles 40*i*, 40*ii*, 40*iii*, preferably along the longitudinal extension direction of the distal end section of the working channel 20. The guiding element 25 extending through the working channel 20 has an engagement section 70. The device 10 is configured so that the guiding element 25 can be selectively coupled—via its engagement section 70—to at least two of the instruments 30*a*, 30*b*, 30*c* in order to guide the instrument 30*a* that is respectively coupled to the guiding element 25 into the region 18 opposite the front side 18 where the instrument 30*a* is to be operated, and/or to move the instrument 30*a* back out of the region 18 toward the front side 16. The device 10 is preferably set up such that the force is transmitted along the longitudinal extension direction 52 of the guiding element 25 for moving the instrument 30*a*, 30*b*, 30*c* into the region 18; and/or the force along the longitudinal extension direction 52 of the guiding element 25 for moving out of the region 18 is transmitted to the instrument 30, 30*b*, 30*c*, via the guiding element 25. Preferably, the device 10 is set up in such a manner that the coupling of an instrument 30*a*, 30*b*, 30*c* to the guiding element 25 and/or the uncoupling of an instrument 3*a*, 30*b*, 30*c* from the guiding element 25 preferably can be controlled outside the body of the patient, while the distal end 44 of the device 10 with the working sections 34*a-c* of the instruments 30*a*, 30*b*, 30*c* is located inside the body of the patient.

Figure 2B:
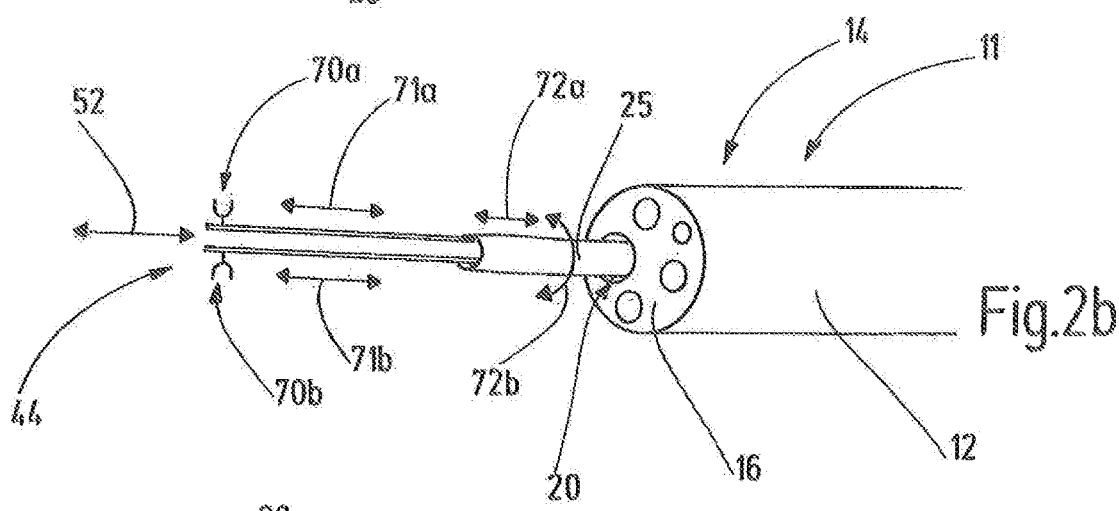

FIG. 2b shows a sectional perspective representation of an exemplary embodiment of an endoscope 11 of the inventive device 10 with a guiding element 25 that can be moved in longitudinal direction in its working channel 20. The guiding element 25 has two engagement sections 70*a*, 70*b* that each can couple to at least one instrument that extends along the shaft 12 in order guide it opposite its front side 16 of the shaft 12. For reasons of clarity, the instruments are not shown in FIG. 2b. The guiding element 25 is configured in such a manner that the working section 34*a*, 34*b* of each of the instruments coupled to the engagement sections 70*a*, 70*b*—as indicated by the double arrows 71*a*, 71*b*—can be moved relative to the working section of the other instrument in longitudinal extension direction 52 of the guiding element 25. Furthermore, the working sections of the instrument coupled to the engagement sections 70*a*, 70*b* can be pivoted relative to each other by rotating and/or pivoting the engagement sections 70*a*, 70*b* about an axis extending along the longitudinal extension direction 52 of the guiding element, and/or be rotated about the axis extending along the longitudinal extension direction 52. In addition, the device 10 is configured such that the guiding element 25 can be slid forward and be retracted as an entity along its longitudinal axis guided in the working channel and be rotated about its longitudinal axis—as indicated by the double arrows 72*a, b*—in order to be able to move the working sections of both instruments accordingly. The force for moving the working sections relative to each other and/or the force for moving the guiding element 25 as an entity can preferably be introduced into the guiding element 25 from outside the body of the patient, while the distal end 14 of the shaft 12 is located in the body of the patient. In doing so, the position of the working section of an instrument relative to the other working section can be changed from outside the body of the patient, while the distal end 44 of the device 10 with the working sections is located inside the body of the patient.

Figure 2C:
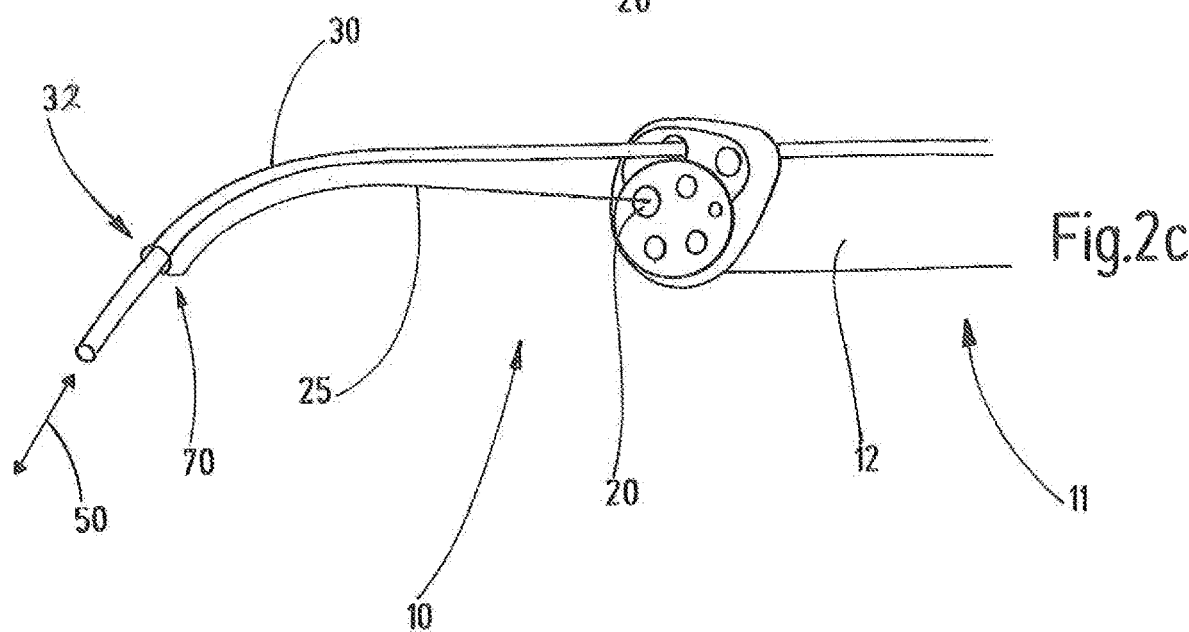

FIG. 2c shows an exemplary embodiment of the device 10 according to the invention with a guiding element 25 that extends through the working channel 20 of the shaft 12 of the endoscope, in which case the guiding element 25 may have a curved end section, for example, where the engagement section 70 of the guiding element 25 is provided. In the engagement section 70, the distal end section 32 of the instrument 30 is guided in a movable manner along a guiding direction 50 that is specified by the engagement section 70. The guiding direction 50 is bent from the longitudinal extension direction of the distal end section of the working channel 20 in order to lead the working section 34 of the instrument 30 in one region away from the imaginary parallel extension of the center axis of the distal end section of the working channel 20.

FIGS. 3ai to 3d show various exemplary embodiments of mounting the guiding element 25 to the engagement element 45. The mounts are suitable for the transmission of force from the guiding element 25 to the instruments 30a, 30b in order to move the working sections 34a, 34b of the instruments 30a, 30b mounted to the engagement element 45, due to the introduction of force into the guiding element 25, away from the outlet side, and/or to move the working sections 34a, 34b of the instruments 30z, 30b back to the outlet side 16. FIGS. 3ai and 3aii show a snap connection for a positive lock between the engagement element 45 and the guiding element 25 transversely with respect to the longitudinal extension direction 52 of the guiding elements 25. The positive lock between the engagement element 45 and the guiding element 25 in longitudinal extension direction 52 of the guiding element is produced in that the section of one connecting part (here: the engagement element 45) with the at least one snap element 75 extends around the other connecting part (here: the guiding element 25) with the snap connection established between opposing positive-locking surfaces 76, said surfaces being provided on the other connecting part, in which case the positive-locking surfaces 76 prevent a movement of one connecting part relative to the other connecting part in the direction 52 of the longitudinal extension of the guiding element 25. Considering the exemplary embodiment according to FIG. 3b, a positive-locking connection is produced transversely with respect to the longitudinal extension direction 52 of the guiding element 25 and in the longitudinal extension direction 52 of the guiding element 25 by a spherical body 77 on the engagement element 45 that is enclosed by two opposing snap tabs 75 when the connection is established. FIG. 3c shows an exemplary embodiment, in which the positive lock is provided in the direction of movement only when the engagement element 45 is slid by means of the guiding element 25 away from the outlet side 16. If, however, the guiding element 25 is retracted, the guiding element 25 can be pulled out of the receptacle in the engagement element 45, in order to disconnect the instruments 30a, 30b from the guiding element 25. In the embodiment according to FIG. 3d, a positive lock is produced in the direction of movement of the guiding element 25 in that a distal end section 57 of the guiding element 25, said end section having a greater dimension relative to an inside dimension of a recess in the engagement element 45, is arranged in the recess. Independent of the specific embodiment, the connection between the instrument 30a, 30b and the guiding element 25 can preferably be disconnected on the distal end of the device in order to allow an instrument change, without necessitating the removal of the instrument 30a, 30b from the device 10.

Figure 4:
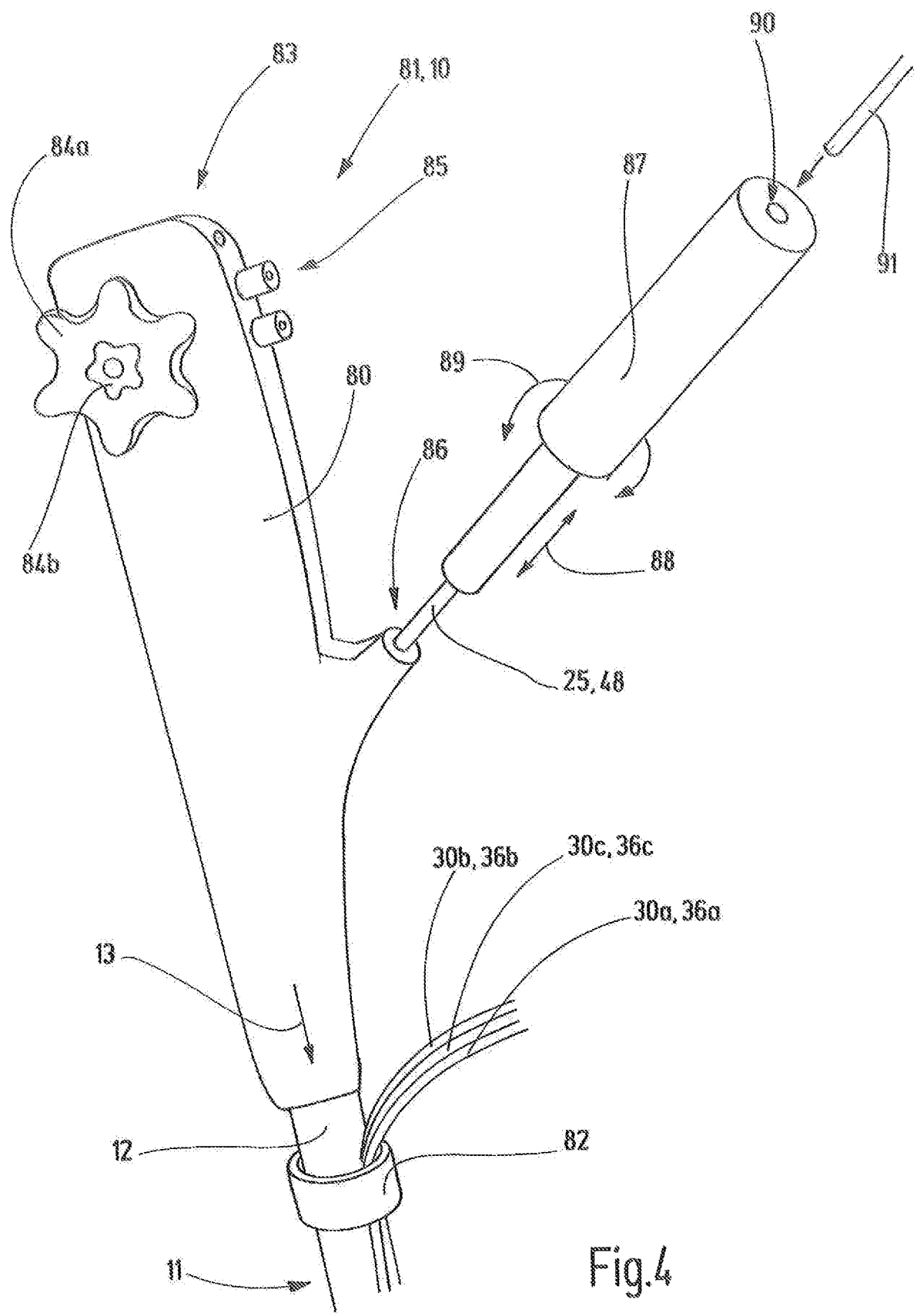

FIG. 4 shows an exemplary handle 80 of a device 10 according to the invention, said handle being arranged on the proximal end 81 of the device 10. The handle 80 is connected to the shaft 12 of the endoscope 11. Around the shaft 12 there is arranged a guide holder 82, adjacent to the handle 80, through which guide holder the functional elements 36a, 36b, 36c extend from the instruments 30z, 30b, 30c up to the working sections 34z, 34b, 34c of the instruments 30a, 30b, 30c on the distal end 44 of the device 10. The handle 80 has a control part 83 for controlling the endoscope 11. For example, the control part 83 may comprise articulating wheels 84a, 84b for the targeted bending of the distal end 14 of the endoscope 11 and control elements 85 for the air and/or water supply, for example, to the distal end 14 of the shaft 12. An inlet 86 into the handle 80 is arranged on the handle 80 which is connected to the working channel 20 through the shaft 12 and through which the guiding element 25 extends into the working channel 20 of the endoscope 11. Fastened to the guiding element 25, there is a guiding element grip 87 arranged on the handle 80, via which the guiding element 25 can be further moved forward in the direction 13 toward the distal end 14 of the shaft 12 and/or the guiding element 25 can be slightly retracted from the inlet 86—as indicated by the double arrow 88. Furthermore, the guiding element grip 87 can be rotated (double arrow 89) in order to rotate the guiding element 25 about the longitudinal axis of the guiding element 25. Thus the engagement section 70, 70a, 70b of the guiding element 25 and/or the engagement element 45 coupled to the guiding element 25 can be moved, positioned and/or oriented relative to the front side 16 opposite the distal front side 16 of the shaft from outside the body of the patient, when the working section 34a-c of the instrument 30a, 30b coupled to the guiding element 25 via its engagement section 70, 70a, 70b and/or via the engagement element 45 is located inside the body of the patient. The guiding element grip 87 itself may optionally be mounted to the handle 80—directly or indirectly via the inlet 86 to the working channel 20—for example by means of a Luer lock connection, in which case the mounted guiding element grip 87 preferably moves along the double arrow 88 for the forward and reverse movements of the instrument 30a, 30b, 30c that is coupled to the guiding element 25, and/or, as indicated by the double arrow 89, can be rotated about a longitudinal axis in order to rotate or pivot the instrument 30a, 30b, 30c that is coupled to the guiding element 25. By mounting the guiding element grip 87, the working channel 20 may be sealed. In the event of an indirect mounting, an adapter is used for mounting to the endoscope 11 and for sealing the working channel 20.

The guiding element 25 may be hollow for guiding fluid, in particular liquid and/or gas, solids and/or an instrument inside the guiding element 25. For example, an opening 90 may be provided on the guiding element grip 87 through which the fluid, in particular liquid and/or gas, and/or solid can be evacuated from the distal end 44 of the device 10 through the guiding element 25 up to the opening 90, and/or the fluid, in particular liquid and/or gas, and/or solid can be brought into the region 18 in front of the front side 16 of the endoscope 11. Alternatively or additionally, an instrument 91 can be slid through the opening 90 by the guiding element 25 into the region 18 in front of the front surface 16 and/or be retracted again from the region 18. The instrument may be, for example, a flexible water jet probe or a liquid jet probe.

The guiding element 25 may be electrically conductive, in which case an electrical power source may be connected to the guiding element 25 outside the body of the patient, said guiding element being configured to supply at least one of the instruments 30a-c that are guided next to the shaft 12 of the endoscope 11.

The device 10 according to the invention can be used to operate as follows: Initially, the instruments 30a, 30b, 30c may be arranged in the position as shown by FIG. 1a, in which the guiding element 25 is in a maximum-retracted position in the working channel 20. The user guides the distal end 14 of the endoscope 11 into the body of the patient. In doing so, the user can adapt the curvature of the distal end 14 of the shaft 12, for example by means of the articulating wheels 84a, 84b on the handle 80. Having arrived at the target, the user can change the position and/or the orientation of the working sections 34a-c of the instruments 30a-30c relative to the distal end 14 of the shaft 12 by introducing a force into the guiding element 25. For example, the user can move the working sections 34a-34c of the instruments 30a-30c in a direction transverse to the front side 16 away from the front side 16, for example in a direction perpendicular away from the front side, by controlling the guiding element 25 from outside the body of the patient, in that the user pushes the guiding element 25 through the working channel 20 further in the direction toward the distal end 14 of the shaft 12. As a result of this, the working sections 34z-c can be arranged, for example, in a position relative to the distal end 14 of the shaft 12, as shown by FIG. 1b. Before and during the treatment or examination in the region 18 in which the working sections 34a-c are located, the user can move the working sections 34a-c by introducing a force into the guiding element 25 in order to adapt the position of the working section 34a-c. To do so, the user can rotate, by rotating the guiding element 25 about its own axis, the working sections 34z-c about this axis. By actuating the guiding element 25, the user can pivot the working sections 34a-c preferably about an axis transversely—in particular perpendicularly—to the longitudinal extension direction of the guiding element 25 in which the guiding element 25 extends outside the working channel. By adapting the position and/or orientation of the working sections 34a-c relative to the distal end 14 of the shaft 12 by means of the guiding element 25, the treatment and/or examination in the region 18 by means of the device 10 can take place preferably under the visual control of the user who can view the region 18 from outside the body of the patient by virtue of the means for image transfer.

The device 10 according to the invention comprises an endoscope shaft 12 through which extends a working channel ending at an outlet side 16 of the shaft 12. A guiding element 25 extends through the working channel 20, said guiding element being preferably guided in longitudinal direction in the working channel 20 along the working channel 20. The device 10 is set up in such a manner that the distal end section 32a-c of an instrument 30, 30a-c extending in longitudinal direction next to the shaft 12 can be moved alongside the shaft 12 beyond the outlet side 16 in order to move the working section 34, 34a-c of the instrument 30, 30a-c away from the outlet side 16 so as to lengthen the distal end section of the device 10. The instrument 30, 30a-c is coupled to the guiding element 25 in order to guide the working section 34, 34a-c of the instrument 30, 30a-30c in a direction transverse to the outlet side 16, for example perpendicular to the outlet side 16, away from the outlet side 16 in a region 18 opposite—this also includes obliquely opposite—the outlet side 16 in order to work with the instrument 30, 30a-c in the region 18. Due to the guiding element 25 that is held and/or guided in the working channel 20, the instrument 30, 30a-30c is indirectly held by the shaft 12 and/or guided by means of the working channel 20 via the guiding element opposite the outlet side 16. Preferably, the device 10 is set up in such a manner that the working sections 34, 34a-d of the instruments 30, 30a-c are shifted and/or pulled away from the outlet side 16 when the working sections 34, 34a-c are moved and/or shifted and/or pulled back to the shaft 12 guided along the longitudinal extension direction of the distal end section 20a of the working channel 20. As a result of this, a particularly stable arrangement of the instrument 30, 30a-c projecting beyond the shaft 12 next to the shaft 12 and/or a particularly stable guiding of the instrument 30, 30a-c beyond the shaft 12 are achieved, said guiding allowing a precise and smooth positioning of the working section 34, 34a-c of the instrument 30, 30a-c.

| List of Reference Signs: | |
|---|---|
| 10 | Device |
| 11 | Endoscope |
| 12 | Shaft |
| 13 | Distal direction |
| 14 | Distal end |
| 15 | Proximal direction |
| 16 | Outlet side, Front side |
| 17 | Illuminating unit |
| 18 | Region |
| 19 | Input of the means for image transmission |
| 20 | Working channel |
| 20a | End section of the working channel |
| 21 | Opening |
| 25 | Guiding element |
| 26 | Longitudinal direction |
| 30 | Instrument |
| 30a | First Instrument |
| 30b | Second Instrument |
| 30c | Third Instrument |
| 32 | Distal End |
| 32a-c | Distal end sections |
| 34 | Working section |
| 34a-c | Working sections |
| 36 | Functional element |
| 36a-c | Functional elements |
| 40 | Guide cuff, first guide holder |
| 40i, 40ii, 40iii | Receptacles |
| 41 | Outside, longitudinal side |
| 42 | Longitudinal extension direction |
| 43 | Second guide holder |
| 44 | Distal end of the device |
| 45 | Engagement element |
| 45a | Positive-locking section |
| 48 | Section |
| 50 | Guiding direction |
| 52 | Longitudinal extension direction |
| 55 | Double arrow |
| 56 | Double arrow |
| 57 | Distal end of the guiding element |
| 60 | Receptacle |
| 61 | Receptacle |
| 65 | Holding element |
| 65a | Positive-locking section |
| 70 | Engagement section |
| 70a, 70b | Engagement sections |
| 71a, 71b | Double arrows |
| 72a, b | Double arrows |
| 75 | Snap element, snap tab |
| 76 | Positive-locking surfaces |
| 77 | Body |
| 80 | Handle |
| 81 | Proximal end |
| 82 | Guide holder |
| 83 | Control part |
| 84a, 84b | Articulating wheels |
| 85 | Control elements |
| 86 | Inlet, input |
| 87 | Guiding element grip |
| 88 | Double arrow |
| 89 | Double arrow |
| 90 | Opening |
| 91 | Instrument |

The invention claimed is:

1. A device (10) with an endoscope (11), wherein a shaft (12) of the endoscope (11) encloses a working channel (20) that opens on an outlet side (16) of the shaft (12), the device comprising:
an instrument (30, 30a, 30b, 30c) that is arranged so as to extend next to the shaft (12), wherein the device (10) is configured such that a distal end section (32, 32a, 32b, 32c) of the instrument (30, 30a, 30b, 30c) containing a working section (34, 34a, 34b, 34c) of the instrument (30, 30a, 30b, 30c) is allowed to be moved along the shaft (12) beyond the outlet side (16) of the shaft (12) in order to move the working section (34, 34a, 34b, 34c) of the instrument (30, 30a, 30b, 30c) into a region located distally from (18) the outlet side (16) of the shaft (12) to allow the working section (34, 34a, 34b, 34c) to operate in the region (18); and a guiding element (25) that extends through the working channel (20) and terminates at a distal end, the guiding element (25) configured to be shifted along a guiding direction (50) defined by the working channel (20) to advance the distal end of the guiding element (25) away from a distal end opening (21) of the working channel (20) and retract the distal end of the guiding element (25) towards the distal end opening (21);

an engagement element (45) comprising a body with a distal facing surface and a proximal facing surface and a through opening extending through the body between the proximal and distal facing surfaces, wherein the through opening is configured to receive the instrument (30, 30a, 30b, 30c) therethrough, wherein the engagement element (45) is releasably connected to the distal end of the guiding element (25) and is configured to be shifted by the guiding element (25) in order to guide the working section (34, 34a, 34b, 34c) of the instrument (30, 30a, 30b, 30c) with the instrument extending through the through opening;

wherein shifting the guiding element (25) distally from the working channel (20) causes the engagement element (45) and the working section (34, 34a, 34b, 34c) of the instrument (30, 30a, 30b, 30c) to be shifted along the guiding direction (50) away from the outlet side (16) of the shaft (12) into the region (18) located distally from the outlet side (16) of the shaft (12);

wherein the guiding element (25) is configured to be disconnected from the engagement element (45) while the distal end of the guiding element (25) and the engagement element (45) are positioned inside a body of a patient by retracting the distal end of the guiding element (25) towards the distal end opening (21);

wherein the guiding element (25) is configured to rotate the engagement element (45) and the working section (34, 34a, 34b, 34c) of the instrument (30, 30a, 30b, 30c) about a longitudinal extension direction (52) of the guiding element (25) and pivot the engagement element (45) and the working section (34, 34a, 34b, 34c) of the instrument (30, 30a, 30b, 30c) relative to a distal end (14) of the shaft (12).

2. The device (10) according to claim 1, wherein the guiding element (25) is guided in the working channel (20) so as to be movable in a longitudinal direction.

3. The device (10) according to claim 1, wherein the guiding element (25) is movably coupled to the instrument (30, 30a, 30b, 30c) in such a manner that the instrument (30, 30a, 30b, 30c), when the guiding element (25) is being moved, is also moved with the guiding element (25).

4. The device (10) according to claim 1, wherein a guide for guiding the instrument (30, 30a, 30b, 30c) along the shaft (12) is provided on a longitudinal side (41) of the shaft (12).

5. The device (10) according to claim 1, wherein the engagement element (45) comprises a second through opening extending through the body of the engagement element between the proximal and distal facing surfaces thereof, wherein the second through opening is configured to receive a second instrument (30a, 30b, 30c) therethrough to allow the second instrument (30a, 30b, 30c) to be guided by the guiding element (25) with the second instrument (30a, 30b, 30c) extending through the through opening.

6. The device (10) according to claim 1, wherein the instrument (30, 30a, 30b, 30c) is allowed to be moved relative to the engagement element (45) within the through opening.

7. The device (10) according to claim 6, wherein the engagement element (45) has at least one of a form matching an outer form of a distal end (14) of the shaft (12), and a form matching a holding element (65) arranged on the distal end (14) of the shaft, so that the engagement element (45) exhibits at least one of: a fixed orientation, a fixed position relative to the distal end (14) of the shaft (12), and a fixed position relative to the holding element (65) when the matching form of the engagement element is in engagement with the outer form of the distal end of the shaft or the holding element.

8. The device (10) according to claim 1, wherein the engagement between the guiding element (25) and the instrument (30, 30a, 30b, 30c) is configured to be released in a non-destructive manner and wherein, after the engagement is released, the guiding element is configured to be brought into engagement in a non-destructive releasable manner with another instrument (30, 30a, 30b, 30c).

9. The device (10) according to claim 1, wherein a guide holder (40) mounted to a distal end (14) of the shaft (12) has receptacles (40i, 40ii, 40iii) in which the instrument (30, 30a, 30b, 30c) is guided in a slidable manner.

10. The device (10) according to claim 1, wherein the guiding element (25) is configured to accommodate at least two instruments (30a, 30b) arranged extending next to the shaft (12), and is at least one of: configured such that the working section (34a, 34b) of at least one of the at least two instruments (30a, 30b) is allowed to be moved relative to the working section (34a, 34b) of the other of the at least two instruments (30a, 30b) guided by the guiding element, and configured such that the working section (34a, 34b) of at least one of the at least two instruments (30a, 30b) is allowed to be at least one of rotated and pivoted relative to the working section (34a, 34b) of the other of the at least two instruments (30a, 30b) by the guiding element (25).

11. The device (10) according to claim 1, wherein the working section (34, 34a, 34b, 34c) of the instrument (30, 30a, 30b, 30c) can be moved back by the guiding element (25) along the guiding direction (50) away from the region (18).

12. The device (10) according to claim 1, wherein the engagement element (45) comprises an opening in the proximal facing surface for receiving the distal end of the guiding element (25) and allowing the guiding element (25) to be disconnected from the engagement element (45) by retracting the distal end of the guiding element (25) out of the opening and towards the distal end opening (21) of the working channel (20).

13. A guiding element (25) for a device (10) according to claim 1.

* * * * *